(12) United States Patent
Lim et al.

(10) Patent No.: US 7,951,880 B2
(45) Date of Patent: May 31, 2011

(54) COMPOSITIONS FOR BREAST IMPLANT FILLING AND METHODS OF USE

(75) Inventors: Tae-Hong Lim, Coralville, IA (US); Joon B. Park, Coralville, IA (US); Jin Whan Lee, Coralville, IA (US); Seok-Jo Yang, Iowa City, IA (US); Jaehyun Kim, Coralville, IA (US); Jin Cheol Cho, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 1109 days.

(21) Appl. No.: 11/299,644

(22) Filed: Dec. 12, 2005

(65) Prior Publication Data

US 2006/0264399 A1    Nov. 23, 2006

Related U.S. Application Data

(60) Provisional application No. 60/635,313, filed on Dec. 10, 2004.

(51) Int. Cl.
  *C08F 116/16*    (2006.01)
  *A61L 27/00*    (2006.01)
  *A61F 2/12*    (2006.01)
(52) U.S. Cl. .............. 526/72; 526/73; 623/87
(58) Field of Classification Search .......... 623/7, 8, 623/926; 526/72, 351, 352, 73
See application file for complete search history.

(56) References Cited

U.S. PATENT DOCUMENTS

| 4,100,627 | A | | 7/1978 | Brill, III | |
|---|---|---|---|---|---|
| 4,173,606 | A | * | 11/1979 | Stoy et al. | 264/2.6 |
| 4,548,981 | A | * | 10/1985 | Kolesinski et al. | 524/555 |
| 4,995,882 | A | | 2/1991 | Destouet | |
| 5,407,445 | A | | 4/1995 | Tautvydas | |
| 5,500,017 | A | | 3/1996 | Bretz | |
| 6,099,565 | A | | 8/2000 | Sakura | |
| 6,162,250 | A | * | 12/2000 | Malice et al. | 623/7 |
| 6,187,044 | B1 | | 2/2001 | Eppley | |
| 6,251,137 | B1 | | 6/2001 | Andrews | |
| 6,287,588 | B1 | | 9/2001 | Shih et al. | |
| 6,312,466 | B1 | | 11/2001 | Robinson, Jr. | |
| 6,413,262 | B2 | * | 7/2002 | Saishin et al. | 606/107 |

(Continued)

FOREIGN PATENT DOCUMENTS

EP    1382313 A1    1/2004

(Continued)

OTHER PUBLICATIONS

Choi et al. "Thermoreversible gelation of poly(ethylene oxide) biodegradable polyester block copolymers. II." Journal of Polymer Science Part A: Polymer Chemistry. 37:13. 2207-2218. 1999.*

(Continued)

*Primary Examiner* — Suzette J Gherbi
(74) *Attorney, Agent, or Firm* — McKee, Voorhees & Sease, P.L.C.

(57) ABSTRACT

The methods and compositions disclosed herein describes a solution containing at least one block co-polymer that is a liquid at lower temperatures and transitions to a gel at higher temperatures. The compositions are useful, for example, as an alternative to saline or silicone-gel as fillers for prostheses.

13 Claims, 7 Drawing Sheets

U.S. PATENT DOCUMENTS

Figure 1A:
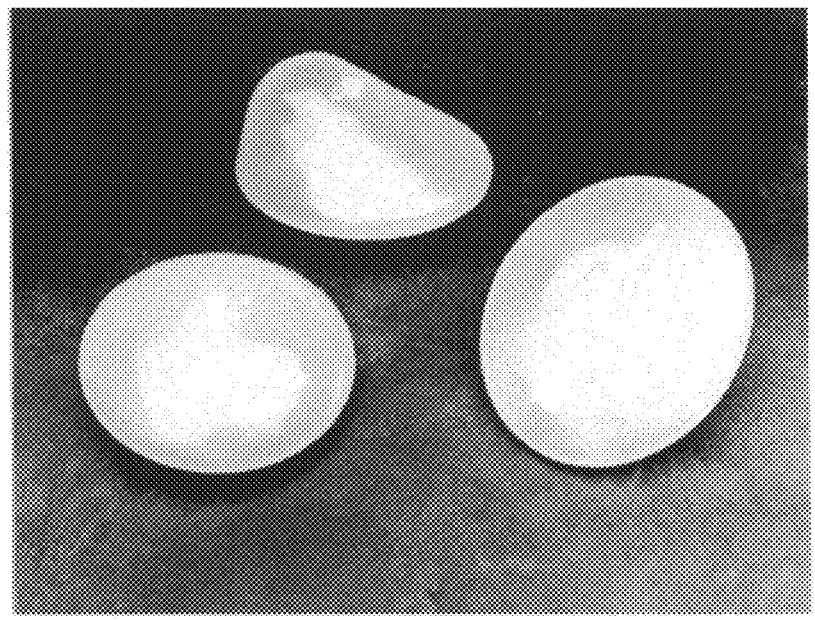

| | | | |
|---|---|---|---|
| 6,426,332 B1 | 7/2002 | Rueger et al. | |
| 6,589,549 B2 | 7/2003 | Shih et al. | |
| 6,660,827 B2 * | 12/2003 | Loomis et al. | 528/354 |
| 6,916,339 B1 * | 7/2005 | Missana et al. | 623/8 |
| 7,217,776 B1 * | 5/2007 | Mallapragada et al. | 526/333 |
| 7,582,311 B1 | 9/2009 | Cleland et al. | |

FOREIGN PATENT DOCUMENTS

| | | |
|---|---|---|
| WO | WO 03/043576 A2 | 5/2003 |

OTHER PUBLICATIONS

Arion, H., "Les hydrogels de carboxy-methyl-cellulose (CMC) pour le remplissage des implants mammaires", Ann Chir Plast Esthét, Feb. 2001, vol. 46 No. 1, pp. 55-59. 2001.

Cunningham, Bruce, "Saline-Filled Breast Implant Safety and Efficacy: A Multicenter Retrospective Review", Plastic and Reconstructive Surgery, May 2000, vol. 105, No. 6 pp. 2143-2151. May 2000.

Eltze, E., "Influence of Local Complications on Capsule Formation Around Model Implants in a Rat Model", J. Biomed Mater. A., vol. 64, No. 1, pp. 12-19, Jan. 2003.

Ersek, Robert, "Bioplastique at 6 Years: Clinical Outcome Studies", Plastic and Reconstructive Surgery, Nov. 1997, vol. 100, No. 6, pp. 1570-1574. Nov. 1997.

Mezzana P., "An Unusual Broken Breast Implant", ACTA Chirurgiae Plasticae 44, 3, 2002, pp. 77-79. 2002.

Rohrich, Rod, "Development of Alternative Breast Implant Filler Material: Criteria and Horizons", Plastic and Reconstructive Surgery, Sep. 1996, vol. 98, No. 3, pp. 553-560. Sep. 1996.

Weinzweig, Jeffrey, "Silicon Analysis of Breast and Capsular Tissue from Patients with Saline or Silicone Gel Breast Implants: II. Correlation with Connective-Tissue Disease", Plastic and Reconstructive Surgery, Jun. 1998, vol. 101, No. 7, pp. 1836-1841. Jun. 1998.

Young, V. Leroy, "Breast Implant Research Where We Have Been, Where We Are, Where We Need to Go", Augmentation Mammaplasty, vol. 28, No. 3, Jul. 2001, pp. 451-483. Jul. 2001.

\* cited by examiner

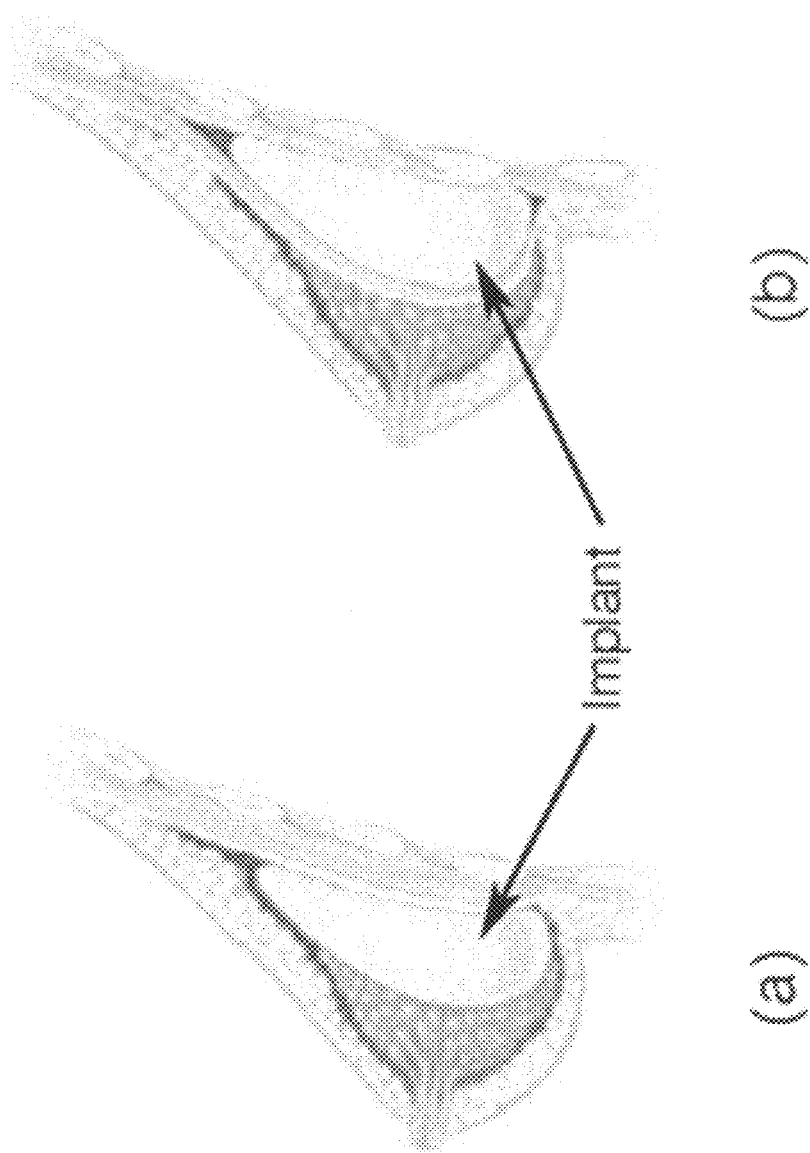

COMPOSITIONS FOR BREAST IMPLANT FILLING AND METHODS OF USE

CROSS-REFERENCE TO RELATED APPLICATIONS

This application claims priority under 35 U.S.C. §119 of a provisional application Ser. No. 60/635,313 filed Dec. 10, 2004, which application is hereby incorporated by reference in its entirety.

FIELD OF THE INVENTION

The present invention relates to a composition for use in a prosthesis and methods of use. More particularly, the present invention relates to filler compositions for soft tissue implants, including breast implants.

BACKGROUND OF THE INVENTION

The present invention is not to be limited to use in breast implants. However, as a manner of convenience and to explain some of the types of problems that the present invention addresses, problems associated with compositions for breast implants are discussed. Millions of women have undergone breast augmentation and reconstruction in the past few decades. Most women choose augmentation to enhance the size and shape of one or both breasts for personal or aesthetic reasons. In contrast, women who undergo a reconstruction procedure want to reconstruct a breast that has been removed, typically for health reasons, such as tumor removal. The reconstruction procedure may vary from a modified radical mastectomy (removal of the underlying muscle as well as the breast), to a simple mastectomy (removal of one breast), to a bilateral mastectomy (removal of both breasts) or to a lumpectomy (removal of a portion of the breast). In either augmentation or reconstruction, the modality intimates the surgical implantation of a breast prosthesis (implant).

Several types of implants are known for breast reconstruction or breast augmentation. These implants often contain an envelope or shell with a closed space that can be filled out with a filler composition.

Conventional implants for treating breast augmentation or reconstruction include a shell or envelope that is filled with a filler composition, for example, silicone gel, saline solution, or other suitable filler. It is desirable that the filler have lubricating properties to prevent shell abrasion, remain stable over long periods of time, and have physical properties to prevent skin wrinkling and implant palpability.

While breast implants containing silicone-gel as a filler are widely used for breast augmentation or reconstruction, a variety of potential disadvantages have been recognized with respect to the stabilization of the implants and the immune system. First, the silicone gel-filled implants have a tendency to leak. In 1992, the FDA issued a voluntary moratorium on silicone gel-filled implants due to public health concerns regarding the potential link between leaking silicone gel-filled implants and autoimmune diseases. Young et al., Plast Reconstr Surg. 1996 September; 98(3):552, 554. To date, the long term effect of silicone-gel on the immune system is still unknown. Second, the leaking of the implants necessitates the need for additional surgeries for removal or repair of the implants. Third, the silicone-gel as a filling material has a greater density than saline or natural tissues which may cause recipients back pain. Lastly, the silicone-gel implant does not mimic the touch and feel of a real breast.

Therefore, many plastic surgeons turned to saline as an answer to silicone-gel problems. Several implants which use saline are known and were found to be advantageous over silicone-gel for several reasons. Saline has a lower density than silicone-gel causing less strain on recipients' backs. In addition, if the implant leaks, the saline solution is non-toxic providing a more tolerated and safer implant than those containing silicone-gel.

However, while the saline implant offer significant advantages over the silicone-gel implant, various problems have been encountered. Implants using saline are disadvantageous in that they frequently result in capsular contraction. Pfleiderer et al., Journal of Biomedical Materials Research, Part A 2003; 64A(1):12, 13. Capsular contraction is a phenomenon where the body forms a lining of fibrous tissue encapsulating the breast implant and the resulting capsule tightens and squeezes the implant. Symptoms range from mild firmness and mild discomfort to severe pain, distorted shape, palpability of the implant, and/or movement of the implant. Additional surgery is needed in cases where pain and/or firmness is severe. This surgery ranges from removal of the implant capsule tissue to removal and possibly replacement of the implant itself. There is no guarantee that capsular contracture will not occur after these additional surgeries.

Saline implants may have to be removed and replaced periodically for other reasons—they fracture or they deflate. Saline, because it is less viscous than silicone-gel, settles in the bottom portion of the implant when the recipient is upright. Young & Watson, Clin. Plast. Surg. 2001; 28(3): 451, 460. This leaves the upper portion of the implant prone to excessive folding or wrinkling, causing stress fracturing of the shell at the fold points. Eresk et al. U.S. Pat. No. 5,067, 965, col. 1; Young & Watson, Clin. Plast. Surg. 2001; 28(3): 451, 460. Furthermore, the saline-filled implants have a tendency to drain gradually in about ten years. See Fallot, U.S. Pat. No. 6,156,066. Barring any deflation or rupture complications, saline as a filler for breast implants produces an unnatural feel and look to the implant. Fallot, U.S. Pat. No. 6,156,066.

In response to the failures of saline and silicone-gel implants, there have been a number of attempts to make a prosthesis filled with a non-toxic filler that that mimics the shape and feel of a natural breast provided by silicone-gel yet is safe to the immune system like saline. Other attempts to provide a safe filler material include polyethylene glycol (Robinson, U.S. Pat. No. 6,312,466), triglycerides (Destourt, U.S. Pat. No. 4,995,882), and even honey (Bretz, U.S. Pat. No. 5,500,017). However, the triglyceride oil disclosed in Destonet et al. or honey disclosed in Bretz fails to provide an implant that is aesthetically pleasing and also duplicates the touch and feel of a natural breast due to the low viscosity of the fillers. Young & Watson, Clin. Plast. Surg. 2001; 28(3): 451, 480.

Due to the limited options and the inadequacy of current fillers to achieve the desired results, there is a need for the current invention.

Accordingly, it is an object of the present invention to provide an effective composition for filling an implant.

It is yet another object of the present invention to provide a composition and method for filling a prosthesis that allows the composition to transition from a liquid to a gel phase at body temperature.

It is another object of the present invention to provide a composition and method for filling an implant which is gelatinous so as to decreases the risk of ruptures due to implant folding.

It is still another object of the present invention to provide a composition and method for filling a prosthesis which reduces leakage and migration of the filler throughout the body.

Another object of the present invention is to provide a composition for filling a prosthesis that closely approximates the touch and feel of a real breast.

These and other objects, features, and other advantages of the present invention will become apparent after a review of the following detailed description of the disclosed embodiments.

SUMMARY OF THE INVENTION

We describe a composition for filling a prosthesis, and in particular a breast implant. In one aspect of the present invention, a filler composition for a breast implant having at least one block co-polymer is provided. The composition is capable of transitioning from a liquid to a gel at temperatures ranging from approximately 22 degrees Celsius (° C.) to approximately 25° C.

In another aspect of the present invention, the filler composition contains a block co-polymer and is capable of transitioning from a gel to a liquid at temperatures less than 26° C.

The filler composition can be prepared by mixing a block co-polymer with sodium hyaluronate or a polysaccharide derivative and solutionizing the co-polymer and sodium hyaluronate or a polysaccharide derivative in deionized water.

In yet another aspect of the present invention, a breast can be augmented or reconstructed by filling a shell or an envelope of an implant with the aqueous filler composition containing at least one block-co-polymer. The composition is capable of transitioning from a liquid to a gel phase at temperatures ranging from approximately 22° C. to approximately to approximately 25° C. The implant may be filled with the composition prior, during, or after implantation into a lumen in a human body.

In still another aspect of the current invention, an implant containing a gel comprised of at least one block co-polymer capable of transitioning from a gel to a liquid phase at temperatures at less than 26° C. may be removed by cooling the breast implant to a temperature less than 26° C. Once the gel composition has transitioned to a liquid, the liquid composition may be removed easily from the implant using standard techniques.

Therefore, compositions with the ability to transition between liquid and gel phases are advantageous as fillers for prostheses, especially for breast implants.

BRIEF DESCRIPTIONS OF THE DRAWINGS

Figure 1B:
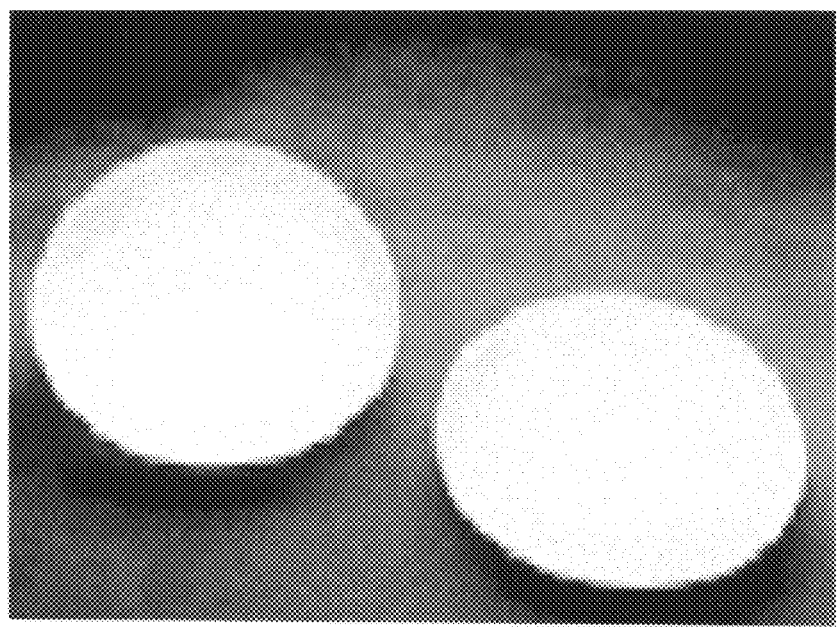

FIG. 1 Silicone gel filled (a) and saline solution filled (b) breast implants. (Modified from ASPS web.[2]) Notice that a patch of polyester (polyethylene tetephthalate, PET) or polytetrafluorethylene (PTFE) felts or cloths are attached for securing the implant in place after tissue in growth.

FIG. 2 Illustrations showing the placement of a breast implant under the existing breast tissue (a) or beneath the chest muscle (b). (Modified from ASPS web.[2])

Figure 3:
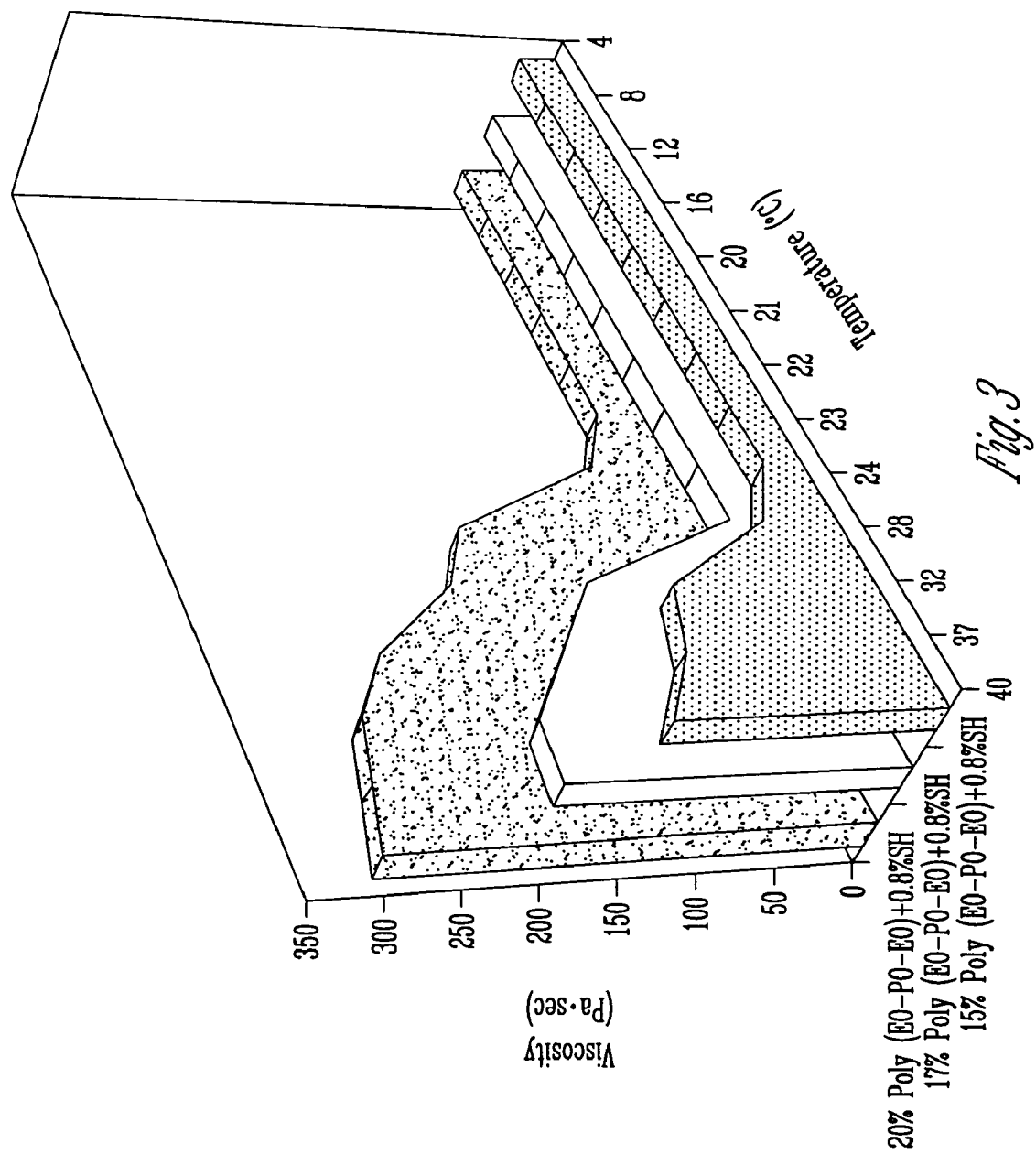

FIG. 3 Viscosity versus temperature data showing that the breast filling implant material becomes more viscous as temperature increases as block co-polymer percentages in the filler material increases.

Figure 4:
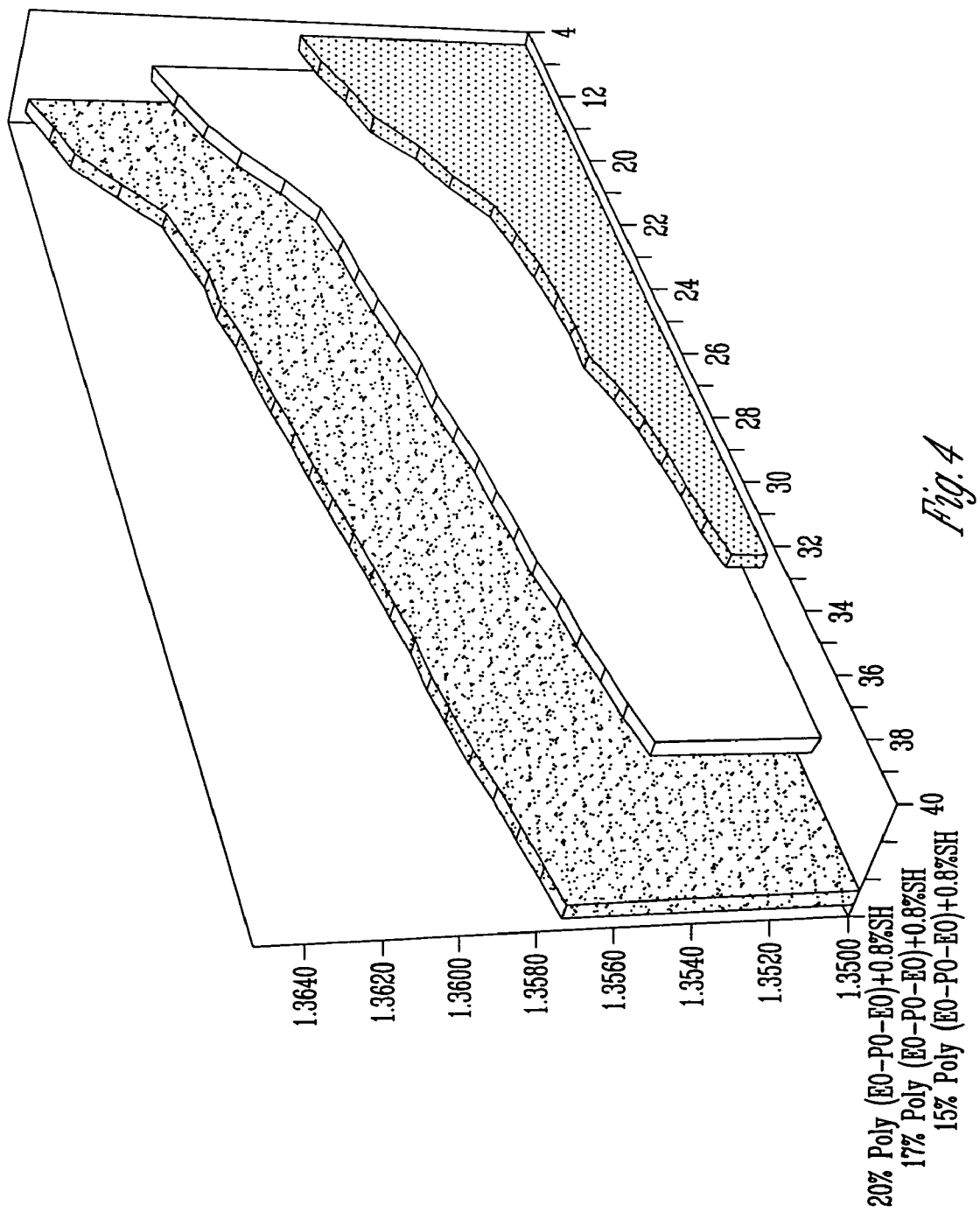

FIG. 4 Refractive index versus temperature data showing that the breast filling implant material becomes more refractive as temperature increases as block co-polymer percentages in the filler material increases.

Figure 5:
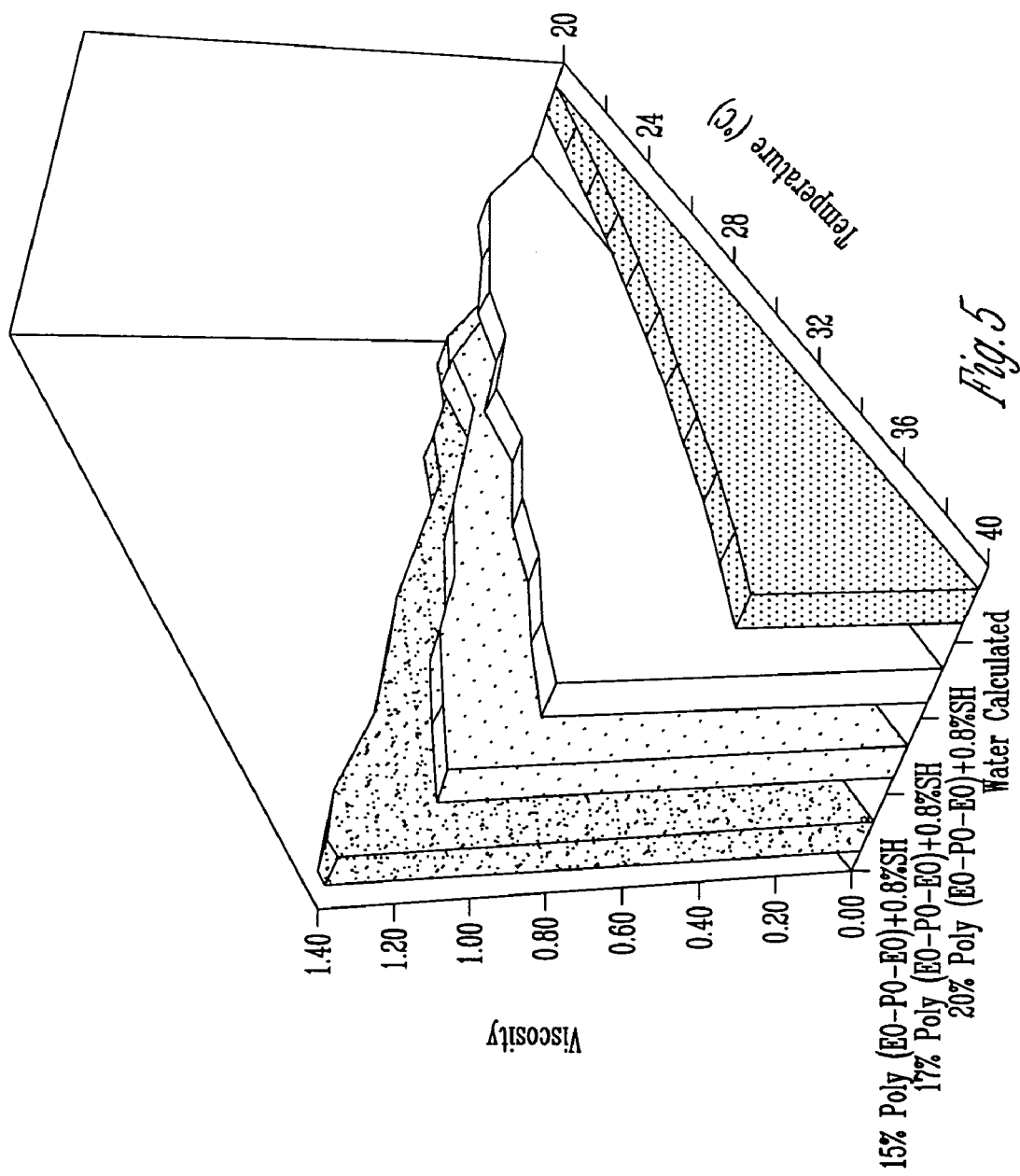

FIG. 5 Percent swelling versus temperature data showing that the swelling ratio versus temperature and percentage of block co-polymer with 0.8% SH the swelling continuously increased with increasing temperature.

Figure 6:
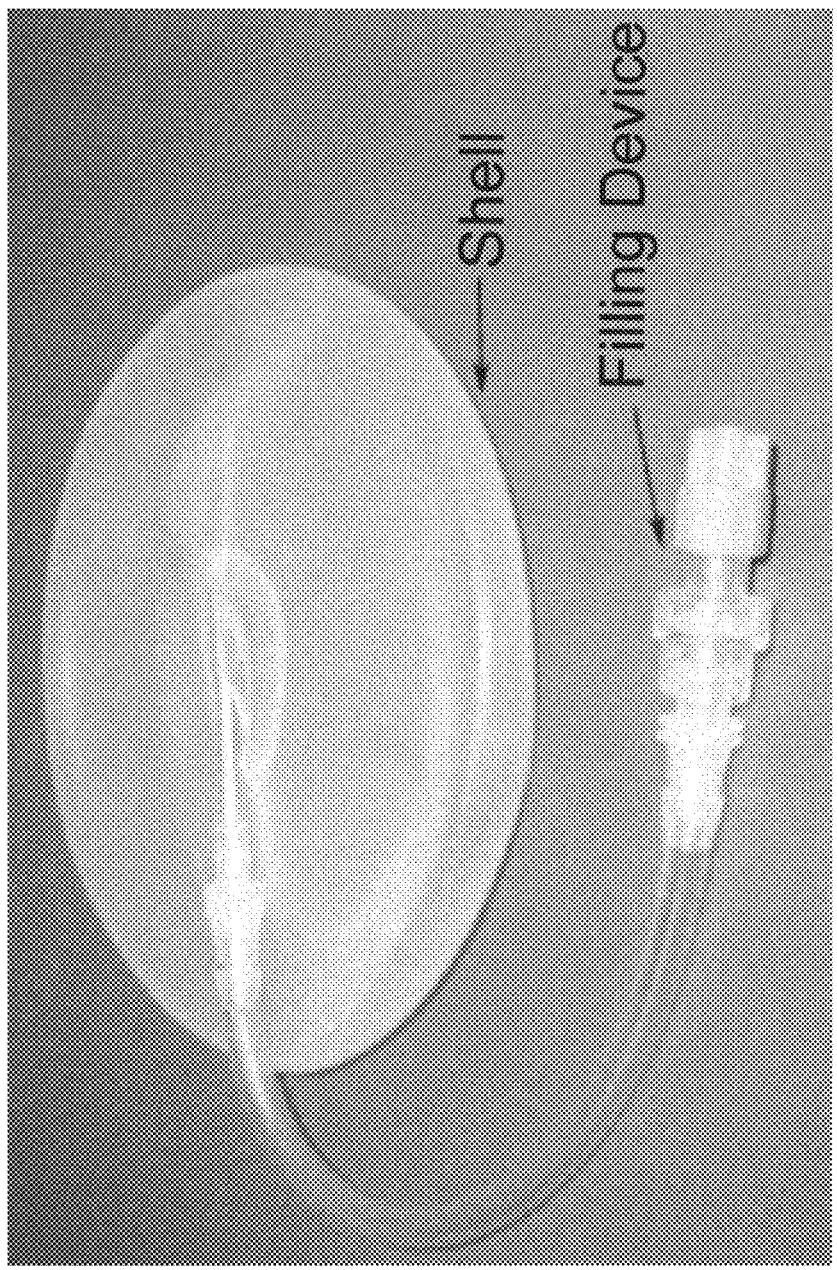

FIG. 6 A breast implant with filling device in place.

Figure 7:
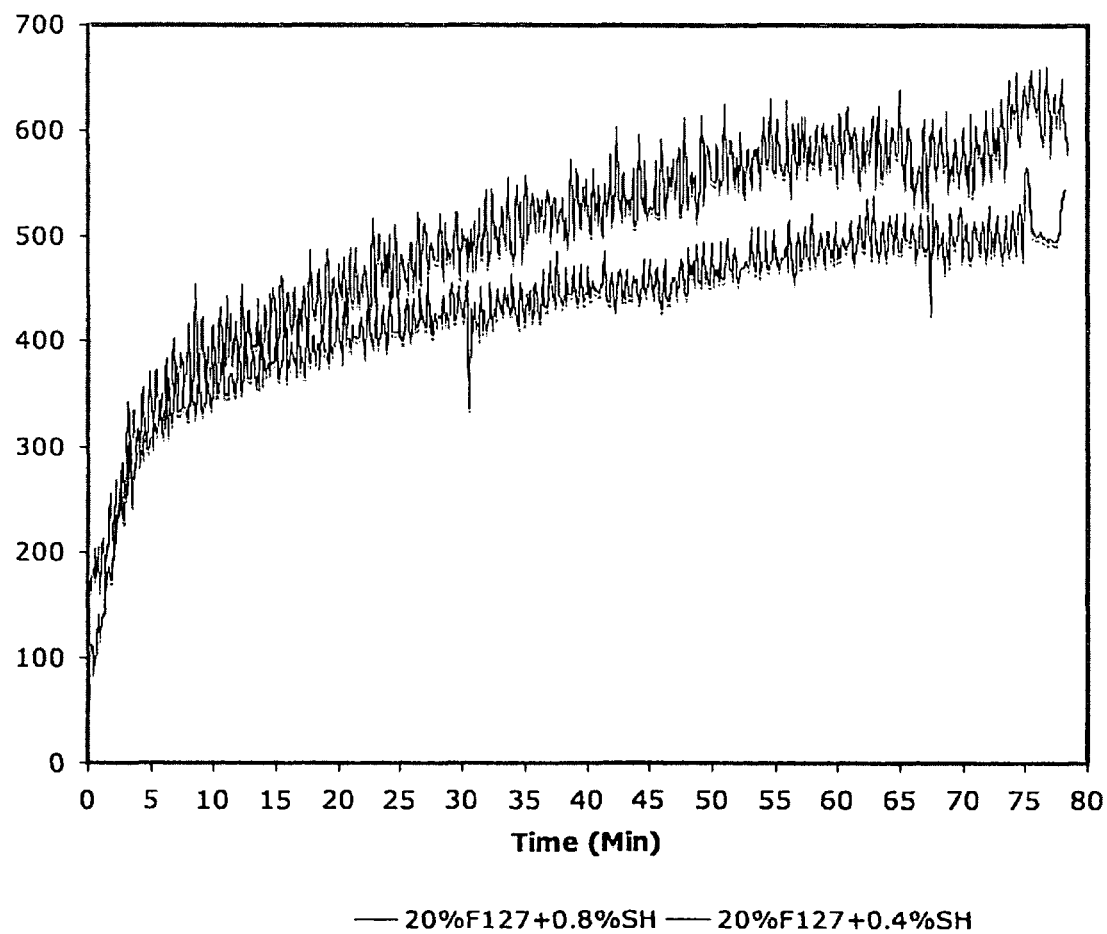

FIG. 7: Gel strengthening effect by viscosity measurement over a time period.

DETAILED DESCRIPTION OF THE INVENTION

The methods by which the objects, features and advantages of the present invention are achieved will now be described in more detail. These particulars provide a more precise description of the invention for the purpose of enabling one of ordinary skill in the art to practice the invention, but without limiting the invention to the specific embodiments described. All references cited herein are hereby expressly incorporated by reference.

The present invention contemplates a composition that is an aqueous solution at low temperatures but transitions to a gel at body temperature. In one embodiment, the aqueous solution contains at least one block co-polymer and is capable of transitioning from a liquid to a gel phase at temperatures ranging from approximately 22° C. to approximately 25° C.

In another embodiment, the composition contains the block co-polymer poly(ethyleneoxide-propyleneoxide-ethyleneoxide) (PEO-b-PPO-b-PEO). Other co-polymers that can be used include a variety of commercial grade polymers, for example, block co-polymers sold under the trademark PLURONICS® produced by BASF Corporation (Mount Olive, N.J.). PLURONICS® are poloxamers, nonionic surfactants that form clear thermoreversible gels in water. The poloxamers are tri-block co-polymers of poly(ethyleneoxide-polypropyleneoxide-polyethyleneoxide) (PEO-PPO-PEO).

In yet another embodiment, the composition also contains sodium hyaluronate. Sodium hyaluronate enhances the physical properties of the block co-polymer because it possesses a strong gelatinous nature, can serve as a lubricant and is easily cross-linkable. The co-polymer is a hydrogel, which entangles physically in situ forming a gel. The sodium hylauronate enhances the physical properties of the co-polymers by acting as a ground substance to provide viscoelastic supplement while block co-polymer acts as a temperature responsive polymer to shift the liquid to the gel (semi-solid) phase.

In another embodiment, collagen or any polysaccharide derivative, for example, alginate, carrageenan, starch, pectin, cellulose, gum Arabic, guar gum, xanthan, pullulan, scleroglucan, dextran, gellan, chitin, chitosan, chondroitin sulfate, heparin, keratin sulfate, and hyaluronic acid, can serve as alternatives to sodium hyaluronate.

In a preferred embodiment, the composition contains at least 15%-40% (w/v) of at least one block co-polymer and at least 0.1-0.8% (w/v) sodium hyaluronate. This composition is prepared by mixing at least 15%-40% (w/v) of one block co-polymer with 0.1-0.8% (w/v) sodium hyaluronate and solutionizing the block co-polymer and sodium hyaluronate in deionized water. As stated previously, collagen or any polysaccharide derivative can be used in place of sodium hyaluronate.

In another embodiment, the composition contains methylcellulose, ethylhydroxyethylcellulose or its analogs, poly (lactic acid-co-glycolic acid)-co-polyethylene (PLGA-co-PEG), in place of a block co-polymer and sodium hyaluronate.

In yet another embodiment, the filler composition contains at least one block co-polymer and is capable of reverse transitioning from a gel phase to a liquid phase at temperatures less than 26° C.

In another embodiment, the composition is included in a shell or envelope for use in an implant. It is envisioned that the present invention may be used in a variety of implants, for example, cheek, chin, bicep, pectoral, calf, buttocks and other soft tissue implants. The present invention is not to be limited to use in breast implants. However, as a manner of convenience and to illustrate some of the types of problems that the present invention addresses, examples using breast implants are described.

Upon the composition's gelation, the implant containing the composition closely approximates the shape and feel of a real breast. Further, the implant containing the composition in a gel phase will not "pucker" or crease. This is advantageous for several reasons. First, it reduces the risk of ruptures. Since the implant is filled with a gel, the implant keeps its shape better. Thus, the implant will not fold or crease as easily, thereby avoiding ruptures from stress-concentration along the folded line. In the case that the implant ruptures, the composition as a gel, rather than as a liquid, minimizes leakage or migration of the composition throughout the body. This facilitates the removal of the "released" composition since it is in a localized area. Third, if there is leakage, an implant filled with the gelled composition will only deflate slightly as compared to an implant filled with an aqueous solution. An implant that slightly deflates is aesthetically less conspicuous than an aqueous-filled implant that partially or entirely deflates.

The Inventors also contemplate that a filler composition for a breast implant may also be comprised of methylcellulose, ethylhydroxyethylcellulose and its analogs, PLGA-co-PEG, in lieu of block co-polymers and sodium hyaluronate.

A breast may be augmented or reconstructed using the present invention. The filler composition is prepared as described previously. The composition in aqueous phase is taken into a syringe in a traditional method or drawn up using a pump system and dispersed into any implant through simple injection. This makes the surgical implantation procedure less invasive since the composition can be introduced into an implant after it is already in place. However, the composition may alternately be introduced into the shell or envelope of an implant prior to or during implantation of the shell or envelope into a lumen in a human body. The Inventors contemplate that the present invention is suitable for use in any implant or prosthesis.

In another embodiment, the composition in a gel phase may be removed from the implant by cooling the implant to a temperature below 26° C. so that the gel undergoes a reversible phase change into an aqueous phase. The aqueous composition can then be removed using a conventional method, for example, a syringe or pump. Thus, the removal of the composition facilitates the removal of the breast implant by decreasing the volume of the implant making the implant easier to manipulate.

Therefore, the present invention of compositions with ability to transition between liquid and gel phases have potential as soft tissue implant fillers. Techniques for manufacturing and filling implants are well known to those of ordinary skill in the art and may be used herein. Although various aspects of the composition and methods are described in detail, it will be apparent to one skilled in the art that modifications, substitutions, and additions may be made without departing from the spirit and scope of the invention. The following examples are described for soft tissue implant filler compositions.

EXAMPLES

Example 1

Formulation of Breast Implant Filling Materials

A block co-polymer of PEO-b-PPO-b-PEO and sodium hyaluronate (SH) are solutionized in a deionized water at an ambient temperature. The block co-polymer is a hydrogel, which interact physically in-situ forming a gel. The SH is added for enhancing the physical properties. It was determined that the in-situ gelling system consisting of 15% to 20% (w/v) of the block co-polymer plus 0.8% (w/v) if SH in deionized water would be the most suitable for our purpose.

Example 2

Liquid-gel Transition Temperature Determination by Viscometer

Liquid-gel transition temperatures were determined by measuring the viscosity at a shear=rate of 1 sec−1 using a viscometer. There was a drastic change in viscosity by varying temperature indicating a liquid-gel transition behavior as shown in FIG. 3. As the amount of block co-polymer increased from 15%, 17%, and 20% (w/v), the gel forming temperatures increased to 22° C., 26° C., and 33° C. respectively.

Example 3

Liquid-gel Transition Temperature Determination by Refractometer

The refractive index was measured for the same polymer solutions by varying temperatures as shown in FIG. 4. The refractive index increased at a higher concentration of the polymer solution, but it was difficult to determine the solution-gel transition temperature for each solution as in the viscosity measurement due to the very small changes in refractive index.

Example 4

Changes in Filler's Volume at Varying Temperatures

Swelling experiments were made in a temperature controlled oven by measuring the volume changes in a graduated cylinder with a telescope. The swelling ratio is defined as V/V20, where V and V20 are the volume at a given temperature and at 20° C. respectively. The swelling ratio of versus temperature and percentage of block co-polymer with 0.8% SH as plotted as shown in FIG. 5. As can be seen, the swelling continuously increased with increasing temperature, although the 15% solution increased more than the others indicating the interaction force between co-polymer chains with medium is less than co-polymer chain to co-polymer chain.

Example 5

Insertion of Prosthesis Containing Filling Material

The shell will be made of poly(dimethyl siloxane) rubber with a provision for the filling fluid. The shell with filling device attached will be implanted first by making a small skin incision as shown in FIG. 6. The shell will then be filled with the new filling material and the filling tube and removed and the connecting device will be detached. The skin will then be closed using standard operating procedures. The polymer liquid will be gelled by the body temperature, making the implant firm.

Example 6

Removal of Prosthesis Containing Filling Material

If the prosthesis is to be removed, it will be cooled by injecting cold water or any source of coldness to room temperature which will liquefy the gel.

Example 7

Effect of the Perfusion Speed on a Heat Flow Rate

The hydrogel consisting of 20% F127 and 0.4% of SH was stored in a refrigerator. The hydrogel (275 ml) controlled at 4° C. was fed into the empty artificial breast shell at 35° C. through a tube with a inner diameter of 0.5 cm at a different pumping rate using the Purfusion pump (Masterflex L/S, Model No. 7524-50, Cole-Parmer Instrument Co.). The time taken for the breast shell to reach out the temperature to 35° C. from 4° C. was measured. Heat flow rate was determined as followed:

$$\text{Heat flow rate} = \frac{\text{Time taken}}{T_f - T_i}$$

where
$T_f$: Final temperature (35° C.)
$T_i$: Initial temperature (4° C.)
Result

TABLE 1

Effect of the perfusion speed on a heat flow rate

| Filling Material | Perfusion Speed (ml/min) | Time Taken (min) | Heat Flow Rate (min/° C.) |
|---|---|---|---|
| Deionized water | 77.25 | 13.0 | 0.42 |
| Sample 1 | 28.56 | 64.0 | 2.06 |
| Sample 2 | 77.25 | 60.5 | 1.95 |
| Sample 3 | 101.4 | 59.5 | 1.70 |

Of among three variations of the perfusion speed using the hydrogel consisting of 20% F127 and 0.4% SH, heat flow rate decreased with increasing perfusion speed. In a comparison of the hydrogel with water at the perfusion speed of 77.25 ml/min, hydrogel was taken about 5 times slower to reach the temperature, compared to deionized water. This means that thermal conductivity of the hydrogel tested here is much lower than deionized water probably because the cross-linking structure of hydrogel is somehow an obstacle against a heat flow.

Example 8

Gel Strengthening Effect by MTS Viscosity Measurement

Method
The different concentrations of hydrogel (20% Pluronic F127+0.4% sodium hyaluronate (SH) and 20% Pluronic F127+0.8% SH) were stored in a refrigerator controlled at 5° C. before testing. Once the syringe containing 10 ml of the hydrogel was quickly placed into the water bath, Mechanical Testing System (MTS) machine (QT/5) was used to push down a plunger of the syringe. The temperature of water bath was maintained at 37° C. and the crosshead of load cell (Maximum limit=1000 lbf) was loaded onto the plunger at a constant speed of 0.81 mm/min. The Poiseuille equation as shown below was used to compute a viscosity of the hydrogel.

$$\mu = \left( \frac{\Delta P \times \pi \times a^4}{8 \times Q \times L} \right)$$

where
$\mu$=viscosity (Pa·sec)
P=pressure (N/m$^2$)
A=radius of the tube (m)
Q=flow rate (m$^3$/sec)
L=length of the tube (m).
The results are shown in FIG. 7.

Both hydrogel formulations increased viscosity over the time period, representing a gel strengthening effect. Under the force exerted to the syringe, viscosity of hydrogel increased significantly within 10 min followed by a steady elevation until making a constant viscosity (588.7 Pa·sec for 20% F127+0.8% SH, 500.8 Pa·sec for 20% F127+0.4% SH) occurred approximately at 55 min for the above line and at 65 min for the lower line. The discrepancy for the absolute value of a viscosity between two samples at a certain time is obvious due to a self-association effect to form a gel at 37° C. This is attributed to the increased concentration of SH while everything else is same.

REFERENCES CITED

U.S. Patent Documents

Eresk et al. U.S. Pat. No. 5,067,965.
Fallot, U.S. Pat. No. 6,156,066.
Robinson, U.S. Pat. No. 6,312,466
Destourt, U.S. Pat. No. 4,995,882
Bretz, U.S. Pat. No. 5,500,017

Other Publications

Young et al. Development of Alternative Breast Implant Filler Material: Criteria and Horizons, Plast Reconstr Surg. 1996 September; 98(3):552-60; discussion 561-2.
Pfleiderer et al. Influence of local complications on capsule formation around model implants in a rat model. Journal of Biomedical Materials Research, Part A 2003; 64A(1):12-19.
Young & Watson. Breast implant research: where we have been, where we are, where we need to go. Clin. Plast. Surg. 2001; 28(3): 451-83, vi.

What is claimed is:
1. A method for augmenting or reconstructing a soft tissue in a body comprising:
introducing a filler composition into a shell or an envelope of a soft tissue implant, the composition comprising an aqueous solution capable of transitioning from a liquid to a gel phase at temperatures ranging from approximately 22° C. to approximately 25° C. and comprising at least one block co-polymer, and wherein the composi- tion is capable of reverse transitioning from the gel phase to the liquid phase by decreasing temperature.

2. The method in claim 1 wherein the method further comprises introducing the composition into the shell or envelope prior to implanting the shell or envelope into a lumen in a human body.

3. The method in claim 1 wherein the method further comprises introducing the composition into the shell or envelope during the implantation of the shell or envelope into a lumen in a human body.

4. The method in claim 1 wherein the method further comprises introducing the composition into the shell or envelope after the implantation of the shell or envelope into a lumen in a human body.

5. The method as defined in claim 1 wherein the block co-polymer comprises poly(ethyleneoxide-propyleneoxide-ethyleneoxide) [purified poloxamer 188 (F127)] (PEO-b-PPO-b-PEO).

6. The method as defined in claim 1 wherein the block co-polymers comprise block co-polymers comprising poly-(ethyleneoxide-polypropyleneoxide-polyethyleneoxide) (PEO-PPO-PEO).

7. The method as defined in claim 1 wherein the composition in claim 1 further comprises: sodium hyaluronate.

8. The method as defined in claim 1 wherein the composition further comprises a collagen or a polysaccharide derivative.

9. The method as defined in claim 8 wherein the polysaccharide derivative is selected from the group consisting of alginate, carrageenan, starch, pectin, cellulose, gum Arabic, guar gum, xanthan, pullulan, scleroglucan, dextran, gellan, chitin, chitosan, chondroitin sulfate, heparin, keratin sulfate, and hyaluronic acid.

10. The method as defined in claim 1 wherein the composition further comprises: at least 15%-40% (w/v) of one block co-polymer.

11. The method as defined in claim 7 wherein the composition further comprises at least 0.1-0.8% (w/v) sodium hyaluronate.

12. The method of claim 1, wherein the gel is capable of reverse transitioning from the gel phase to the liquid phase at temperature of less than 26° C.

13. The method of claim 1, wherein the block co-polymer is temperature responsive and capable of transitioning the composition from the gel phase to the liquid phase.

* * * * *